United States Patent [19]

Shimomura et al.

[11] Patent Number: 5,128,088
[45] Date of Patent: Jul. 7, 1992

[54] CONTINUOUS METHOD FOR MAKING ADHESIVE-LINED MALE EXTERNAL CATHETERS

[75] Inventors: Gary D. Shimomura, Chicago; Eric D. Ellingson, Schaumburg, both of Ill.

[73] Assignee: Hollister Incorporated, Libertyville, Ill.

[21] Appl. No.: 567,111

[22] Filed: Aug. 14, 1990

[51] Int. Cl.⁵ .................. B28B 1/38; B05D 3/00; A61F 5/453
[52] U.S. Cl. .................. 264/305; 156/289; 264/130; 264/304; 427/273; 604/352
[58] Field of Search .......... 604/352, 351, 349; 264/304–306, 130, 131; 427/271, 273, 277, 272, 337; 427/208.6; 156/289, 294, 293

[56] References Cited

U.S. PATENT DOCUMENTS

| | | | |
|---|---|---|---|
| 2,960,414 | 11/1960 | Gustin et al. | 427/273 |
| 3,788,324 | 1/1974 | Lim | 604/352 |
| 3,817,809 | 6/1974 | Dereniuk | 156/296 |
| 4,475,910 | 10/1984 | Conway et al. | 604/349 |
| 4,769,099 | 9/1988 | Therriault et al. | 604/352 |

FOREIGN PATENT DOCUMENTS

| | | | |
|---|---|---|---|
| 86/00816 | 2/1986 | PCT Int'l Appl. | 604/349 |
| 89/01324 | 2/1989 | PCT Int'l Appl. | 604/349 |

Primary Examiner—Michael W. Ball
Assistant Examiner—Daniel J. Stemmer
Attorney, Agent, or Firm—Tilton, Fallon, Lungmus

[57] ABSTRACT

A continuous method for making adhesive-lined condom catheters for male urinary drainage. The method involves successive steps carried out with respect to a dipping mandrel and a latex catheter being formed upon it, all of which may be performed automatically as the mandrel is advanced from one station to the next.

4 Claims, 1 Drawing Sheet

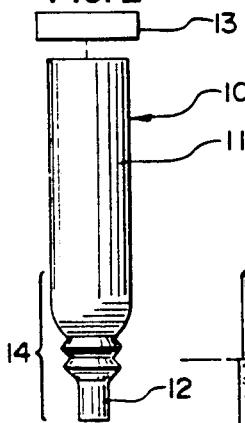
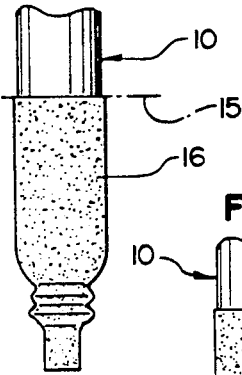
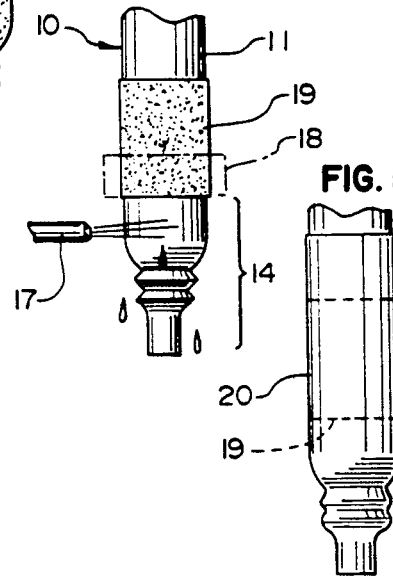
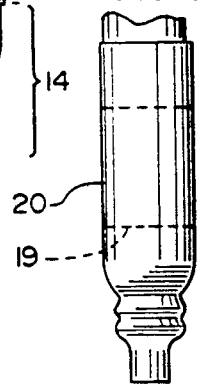
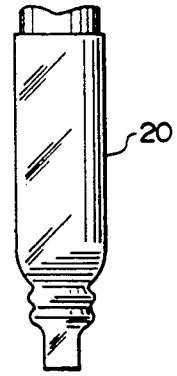
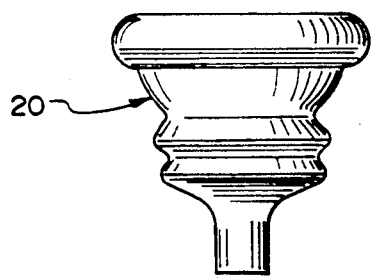
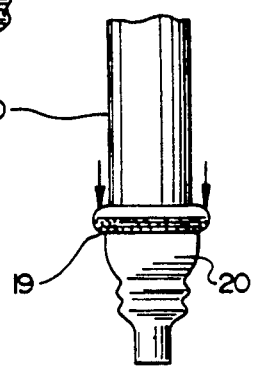

CONTINUOUS METHOD FOR MAKING ADHESIVE-LINED MALE EXTERNAL CATHETERS

BACKGROUND AND SUMMARY

Male external catheters are commonly formed by dipping a mandrel into latex baths and curing the latex between successive dipping operations to build up a catheter wall of desired thickness. Thereafter, the catheter is removed, usually by rolling it off of the mandrel so that it assumes a rolled condition in which it is subsequently marketed.

While the latex-dipping steps are conventional and are similar to those carried out in the manufacture of latex gloves, the further requirement that such a catheter be internally lined with a band of pressure-sensitive adhesive complicates manufacturing operations. Further complications arise from the fact that the provision of such an adhesive coating also requires the outer surface of the catheter to be treated with a suitable release agent so that when the catheter is rolled into its marketed form it may later be unrolled by the user.

The extent of such complexities is illustrated by published International Application WO 86/00816 based on PCT application PCT/DK85/00068. There the steps of applying the inner adhesive layer and the outer release layer are performed only on a pre-formed catheter. In one version an adhesive strip 5 is first wrapped about a mandrel 7 having ducts for the discharge of air under pressure (FIG. 5). A catheter is fitted upon the mandrel while air is simultaneously discharged from the ducts to expand the catheter and prevent its inner surfaces from prematurely contacting the adhesive strip. When the catheter is in place, the flow of air is discontinued and the catheter is allowed to contract into contact with the adhesive. Thereafter, a release layer strip 6 is wrapped about the outer surface of the catheter, and the catheter is finally rolled off of the mandrel. It is believed apparent that such manufacturing operations are labor-intensive and involve complex manipulation that are not easily automated.

U.S. Pat. No. 4,475,910 also discloses a manufacturing method in which an inner adhesive layer and an outer release layer are applied to a pre-formed catheter. In that method, the release layer is first applied to the outer surface of a catheter supported by a mandrel and, after the release layer is cured, an adhesive layer is also applied to the outer side of the catheter over the release layer. The patent does not specify just how the pressure-sensitive adhesive layer is applied but, since no mention is made of drying or curing the adhesive, that layer is presumably transferred to the catheter in its final tacky state from an adhesive-bearing transfer strip or the like. While simpler than the procedure described in the aforementioned British application, the methodology disclosed in this patent nevertheless involves steps that are difficult to automate.

Accordingly, a main aspect of this invention lies in providing a method which may be readily automated and performed on a continuous basis (in contrast to batch basis). In its simplest form, a mandrel is exposed to a series of dipping and drying (or curing) steps for purposes of forming the latex catheter and the adhesive and release layers o its opposite surfaces.

A distinctive feature of the method of this invention lies in applying a layer of adhesive, preferably by means of a dipping operation, directly to the non-stick surface of a mandrel during the first step of the manufacturing procedure. Thereafter, by a series of dipping and curing steps, a latex catheter is formed on the same mandrel over the layer of previously-applied adhesive. Following curing of the latex, the mandrel is again dipped, this time in a bath of release agent, to coat the outer surface of the catheter and prevent the adhesive from adhering to the catheter's outer surface when the finished catheter is rolled off of the mandrel.

Therefore, in brief, the method involves the steps of applying a medical-grade, pressure-sensitive adhesive to the release surface portion of a rigid mandrel to form a weakly-adhering adhesive coating thereon, then dipping the mandrel into a latex bath to form a first latex layer over the mandrel and the adhesive coating and curing the latex layer, repeating the latex dipping and curing steps until a desired wall thickness for the catheter has been formed, then dipping the mandrel in a silicone bath to form a release coating upon the catheter, and finally curing the release coating and rolling the finished catheter off of the mandrel.

Other features advantages, and objects of the invention will become apparent from the specification and drawings.

DRAWINGS

FIG. 1 is a flow chart setting forth the basic steps of the method of this invention for making adhesive-line catheters.

FIGS. 2-7, inclusive, are schematic views depicting certain of the steps of this method.

FIG. 8 is an enlarged side elevational view illustrating a finished catheter made in accordance with the method of this invention.

DETAILED DESCRIPTION OF PREFERRED EMBODIMENTS

All of the method steps described herein are performed in relation to a mandrel o form 10 of the type depicted in FIG. 2. Such a mandrel typically has a cylindrical body portion 11 and a reduced end portion 12. Suitable supporting means 13 supports the mandrel and advances it into and through the successive treatment stations although, theoretically, such supporting and advancing functions might also be performed manually. While each catheter may be totally manufactured on a single mandrel, as described herein, it is also to be understood that there may be special circumstances making it more desirable to transfer a catheter from one mandrel to another at some point in the sequence of fabrication steps.

The first step involves the applying of adhesive 16 directly to the surfaces of the mandrel. Such application is preferably, but not necessarily, performed by means of a dipping operation in which the mandrel is supported in vertical condition with its reduced end 12 facing downwardly and is then lowered into a bath of liquid adhesive. The surfaces of the mandrel should be capable of being wetted by the adhesive but should nevertheless resist sticking of the adhesive during the final stages of catheter manufacture. More specifically, the non-stick surface of the mandrel and the composition of the adhesive should be formulated so that the adhesive will adhere weakly to the mandrel but may later be stripped away without leaving an adhesive residue on the mandrel. With the preferred adhesives described hereinafter, it has been found effective to utilize an aluminum mandrel coated either with silicone or with polytetrafluoroethylene. It has also been found effective to form the mandrel entirely of polytetrafluoroethylene.

The preferred adhesive is an acrylic emulsion adhesive although other water-based medical-grade adhesives, such as a rubber-based emulsion or a resin emulsion, might be used. One adhesive that has been found effective is an acrylic emulsion adhesive from Ashland Chemical Company, Cincinnati, Ohio, sold under the designation Aroset 2177-W-59. Another emulsion adhesive that is believed suitable is available from U.S. Adhesives Corporation, Chicago, Ill., under the designation PSA 218. To promote application, effective draining, and more rapid curing or drying, the adhesive should preferably be diluted to a viscosity of 300 to 700 centipoises (CPS), at least if application is to be by means of dipping. It is believed that most acrylic emulsion adhesives in the forms they are commercially available are too viscous for this purpose. It has been found that such adhesives should be diluted with water to approximately 45% solids to achieve the viscosity levels indicated. While temperature of application is not particularly critical (the application may occur at room temperature), humidity should be 60% or less in order to facilitate subsequent curing or drying of the adhesive.

Following the adhesive-applying step, the cured pressure-sensitive adhesive should cover only a portion of the surface of cylindrical body 11. Specifically, the reduced end portion 12, and the adjoining lower portion of cylindrical body 11 (as designated by numeral 14 in FIG. 2) should be free of adhesive at the conclusion of the adhesive coating operation. While a selective application of adhesive only to that portion of the mandrel above section 14 might be achieved by a precisely-directed spraying procedure or by dipping the mandrel in upright condition (with its reduced end facing upwardly), or even by transferring a layer of adhesive to the mandrel by means of a transfer strip, roller, or other type of applicator, it has been found convenient and highly effective to perform all operations with the mandrel in the inverted condition shown and to carry out the adhesive-coating step in two stages, the first stage being a dipping stage (FIG. 3) and the second being a partial removal stage (FIG. 4).

In the dipping stage, the mandrel 10 is dipped into liquid adhesive to a level 15 indicated in FIG. 3. Thereafter, while the adhesive is still wet i.e. uncured, section 14 of the mandrel is exposed to a solvent spray from one or more nozzles 17 to rinse away all adhesive upon that section. A suitable shield 18 may be used to prevent the solvent from contacting the adhesive applied to the mandrel directly above section 14. The result is that the mandrel is left with an adhesive band 19 that extends about that portion of the cylindrical body 11 directly above section 17.

Where the adhesive is a water-based acrylic adhesive, the solvent that flushes away adhesive from section 14 may be water. To insure complete removal of the adhesive, a cleaning agent may be included in the water spray or, alternatively, the lower section 14 of the mandrel may be dipped into an ultrasonic bath containing such a cleaning solution such as, for example, an aqueous solution of a surfactant such as 1% Triton X 100.

Where the adhesive is applied in a liquid state, as in the manner described above, such adhesive must be cured before further coating procedures are undertaken. Since the pressure-sensitive adhesive in its final condition will remain tacky, the term "curing" is used here even though the transition from a liquid to a sticky, semi-solid condition is essentially the result of a drying process. To promote more uniform curing or drying, it is preferable to perform the operation in two stages. In the first, the mandrel is advanced into (and through) a heating chamber maintained at a lower temperature range between 55° to 115° F.; in the second, the heating temperature falls within the range of 155° to 215° F. The total two-stage heating period may last approximately three minutes depending, of course, upon the adhesive selected, its viscosity, and the thickness of the coating.

It has been found beneficial to apply a release agent to the cleansed lower section 14 of the mandrel either just prior to the heating operation or at an intermediate point in that operation. For example, such a release agent may be advantageously applied between the first and second stages of a heating operation. The second heating stage therefore performs the dual functions of completing the curing of the adhesive and drying the release agent applied to mandrel section 14 beneath the adhesive.

The release agent is preferably applied by dipping and may be any suitable agent capable of preventing latex from securely adhering to section 14 in subsequent manufacturing operations. The dipping bath of release agent may, for example, take the form of a 10% aqueous solution of calcium stearate. A solution of zinc stearate may also be used. Alternatively, the lower section 14 of the mandrel may be dipped into an aqueous bath containing talc.

With the adhesive band 19 in place upon mandrel 10, and with section 14 of the mandrel treated with a suitable release agent, the mandrel is then subjected to a sequence of dipping steps that result in the formation of a latex sheath upon the mandrel's surface. Since latex dipping procedures are well known in the art, and since such procedures may be varied considerably depending on factors such as sheath design and intended wall thickness, only a general disclosure of such procedures will be given here. While the percentage of solids in the latex dipping bath may be less critical, effective results have been obtained where the percentage of solids is also approximately 45%.

Latex is cured by drying and coagulation, so a coagulating agent must be used. A typical agent is calcium nitrate (e.g., an aqueous 35% solution) although any of a number of nitrates might be used. Acids may also be used for latex coagulation and, as well known, such coagulation is promoted by the application of heat.

The coagulating agent may be applied by dipping and such dipping may occur before the latex dip, or after the latex dip, or both before and after the latex dip. However, if treatment with a coagulating agent occurs prior to the first latex dip, care should be taken to avoid contact between the coagulating agent and adhesive band 19 since such contact may adversely affect the adhesion between band 19 and the latex applied thereover. Therefore, if exposure to coagulant precedes the first latex dip, the only portion of the mandrel exposed to coagulant should be section 14.

FIG. 5 shows the mandrel 10 after the first latex dip in which a thin layer of latex 20 covers the mandrel downwardly from a level above the upper margin of adhesive band 19. The latex is then cured, or partially cured, by dipping the mandrel to the same extent in a coagulant bath (e.g., aqueous 35% calcium nitrate solution) and allowing the coagulant to partially dry. While theoretically a sheath might be formed with only a single latex dip followed by coagulant exposure, a repetition of the latex and coagulant dipping steps is usually required to achieve the desired wall thickness. In any event, once the desired thickness has been attained, the latex is allowed to gel and the sheath 20 is then dipped into a water bath to leach out excess salts and soluble impurities. Thereafter, the sheath is allowed to fully cure and, for that purpose, may be heated in a suitable oven at a temperature within the general range of 100° to 250° F. A two-zone drying oven has been found particularly effective, the first zone operating at temperatures from 140° to 180° and the second zone at temperatures from 200° to 240°.

Following the curing and cooling of the latex sheath, the mandrel is dipped into a bath to coat the entire outer surface of the sheath with a suitable release agent. While various agents might be used, a silicone bath containing 7 to 9% solids in a trichloroethane solvent has been found particularly effective. FIG. 6 schematically depicts the sheath 20 after it has been withdrawn from such a bath and the silicone coating has been cured by heating it at a temperature within the range of 70° to 90° C.

The sheath is then rolled off of the mandrel (FIG. 7), carrying with it on its inside surface the adhesive layer 19 previously applied to the mandrel. The silicone release coating on the sheath's outer surface prevents the adhesive 19 from clinging to that surface when the sheath is later unrolled. The finished sheath or catheter is depicted in FIG. 8.

While in the foregoing we have disclosed embodiments of the invention in considerable detail for purposes of illustration, it will be understood by those skilled in the art that many of these details may be varied without departing from the spirit and scope of the invention.

We claim:

1. A method for making male external catheters with adhesive-coated inside surfaces by means of a vertically-oriented, rigid, dipping mandrel having a generally cylindrical body portion and a reduced lower end portion, comprising the steps of: applying a heat-curable, pressure-sensitive adhesive to surfaces of said body portion and said reduced lower end portion to form a weakly-adhering, pressure-sensitive adhesive coating thereon; then, while said coating is uncured, washing away said coating from said surfaces of said lower end portion and a part of said body portion adjacent thereto while leaving a band of said adhesive coating about a part of said cylindrical body portion thereabove; then curing said adhesive of said band; then dipping said mandrel into a latex bath to form a first latex layer over said mandrel and said band of adhesive coating and exposing said first latex layer to a coagulating agent and heat; repeating said latex dripping step to form at least one further latex layer over said first latex layer and also exposing said further layer to a coagulating agent and heat; drying said latex layers to provide a dry, multi-layered latex catheter supported by said mandrel; dipping said mandrel in a silicone bath to form a release coating upon said catheter; and curing said silicone release coating.

2. The method of claim 1 in which there is the further step of rolling said catheter off of said mandrel with said band of pressure-sensitive adhesive coating releasing from said mandrel and adhering to said catheter's inner surface.

3. The method of claims 1 or 2 in which said step of applying said adhesive to said mandrel includes dipping said mandrel into a bath of liquid pressure-sensitive adhesive.

4. The method of claim 1 in which there is the step of applying a release agent to the surfaces of said mandrel below said adhesive band following said washing step and prior to dipping said mandrel in a latex bath.

* * * * *